(12) United States Patent
Leander et al.

(10) Patent No.: US 8,227,017 B2
(45) Date of Patent: Jul. 24, 2012

(54) SYSTEM AND METHOD FOR ENHANCING THE EFFICACY OF ANTIMICROBIAL CONTACT LENSES AND OTHER SURFACES

(75) Inventors: Susan Leander, Gainesville, FL (US); William Toreki, Gainesville, FL (US); Gerald Olderman, Bedford, MA (US); Albina Mikhaylova, Gainesville, FL (US)

(73) Assignee: Quick-Med Technologies, Inc., Gainesville, FL (US)

( * ) Notice: Subject to any disclaimer, the term of this patent is extended or adjusted under 35 U.S.C. 154(b) by 89 days.

(21) Appl. No.: 12/742,923

(22) PCT Filed: Nov. 13, 2008

(86) PCT No.: PCT/US2008/083410
§ 371 (c)(1), (2), (4) Date: May 14, 2010

(87) PCT Pub. No.: WO2009/064890
PCT Pub. Date: May 22, 2009

(65) Prior Publication Data
US 2010/0255178 A1    Oct. 7, 2010

Related U.S. Application Data

(60) Provisional application No. 60/987,513, filed on Nov. 13, 2007.

(51) Int. Cl.
*B05D 3/10* (2006.01)
*A61K 9/08* (2006.01)
*G02C 7/04* (2006.01)

(52) U.S. Cl. ........ 427/2.24; 427/2.1; 427/335; 424/429; 351/159

(58) Field of Classification Search ............. 427/2.1, 427/2.24, 331, 337; 424/429
See application file for complete search history.

(56) References Cited

U.S. PATENT DOCUMENTS

| | | | |
|---|---|---|---|
| 4,443,429 A | 4/1984 | Smith et al. | |
| 4,675,347 A | 6/1987 | Mochizuki et al. | |
| 5,037,647 A * | 8/1991 | Chowhan et al. | 424/78.04 |
| 5,515,117 A | 5/1996 | Dziabo et al. | |
| 5,520,910 A | 5/1996 | Hashimoto et al. | |
| 6,146,688 A | 11/2000 | Morgan et al. | |
| 6,475,537 B1 * | 11/2002 | King et al. | 424/778 |
| 6,534,075 B1 | 3/2003 | Hei et al. | |
| 6,702,983 B2 | 3/2004 | Hu et al. | |
| 6,805,836 B2 * | 10/2004 | Salamone et al. | 422/1 |
| 7,001,873 B2 | 2/2006 | McDonnell et al. | |
| 7,045,673 B1 | 5/2006 | Batich et al. | |
| 7,151,139 B2 | 12/2006 | Tiller et al. | |
| 2002/0177828 A1 | 11/2002 | Batich et al. | |
| 2003/0117579 A1 * | 6/2003 | Morris et al. | 351/200 |
| 2005/0008670 A1 * | 1/2005 | Cobham | 424/411 |
| 2005/0033251 A1 | 2/2005 | Toreki et al. | |

FOREIGN PATENT DOCUMENTS

| | | |
|---|---|---|
| KR | 100420850 | 2/2004 |
| WO | 2004/030715 | 4/2004 |
| WO | 2007/024974 | 3/2007 |

OTHER PUBLICATIONS

Chang, D.C., et al, "Multistate Outbreak of Fusarium Keratitis Associated With Use of a Contact Lens Solution," JAMA 296(8) p. 953-963 (2006).

\* cited by examiner

*Primary Examiner* — Timothy Meeks
*Assistant Examiner* — Cachet Sellman
(74) *Attorney, Agent, or Firm* — Gerry J. Elman; Elman Technology Law, P.C.

(57) ABSTRACT

A system and method of enhancing the antimicrobial and biofilm-resistant efficacy of surfaces that have cationic polyelectrolytes nonleachably bound thereto in order to impart antimicrobial activity to the surface. The system for enhancing antimicrobial efficacy involves brushing, dipping, wiping, spraying, or storing the surface in a solution containing citrate ion. The method involves treatment of the surface with a solution which enhances the antimicrobial and biofilm-resistant efficacy of the surface, and which prevents a loss of the antimicrobial properties of the surface which may occur over time. Preferably, the enhancement agent is citrate ion and the cationic polyelectrolyte is poly(diallyldimethylammonium chloride), also known as polyDADMAC. The system is particularly beneficial for surfaces of articles such as contact lenses.

15 Claims, No Drawings

SYSTEM AND METHOD FOR ENHANCING THE EFFICACY OF ANTIMICROBIAL CONTACT LENSES AND OTHER SURFACES

CROSS REFERENCE TO RELATED APPLICATIONS

This application is a National Stage entry into the United States under 35 U.S.C. §371 of our co-pending International Application, Serial Number PCT/US2008/083410, filed Nov. 13, 2008, which is a non-provisional application of U.S. Provisional Application No. 60/987,513, filed Nov. 13, 2007 and claims benefit of priority to both prior applications. The disclosures of our International Application Number PCT/US2008/083410 and our Provisional Application No. 60/987,513 are hereby incorporated by reference.

TECHNICAL FIELD

This invention relates to contact lenses and other articles with one or more surfaces having cationic polyelectrolytes nonleachably bound to the surfaces to impart antimicrobial activity. This invention also relates to a system and method for enhancing the antimicrobial activity and increasing biofilm resistance of the surfaces, wherein the antimicrobial surfaces are stored in or rinsed with solutions containing specific ions.

BACKGROUND ART

Contact lenses, either hard or soft, especially those designed for extended wear, have been associated with bacterial infections of the eye, as bacteria and fungi can easily colonize the contact lens and grow between the contact lens and the cornea in an environment that provides adequate moisture, favorable temperature and suitable nutrients. Bacterial keratitis, commonly associated with contact lens wear, is a destructive disease of the cornea that is often caused by *Pseudomonas aeruginosa*. The creation of an antimicrobial contact lens that can prevent colonization and reduce the bacterial load, especially at the cornea/lens interface, could result in a reduction in the incidence of serious eye infections.

Hard contact lenses tend to mechanically damage the cornea. This allows microorganisms to invade and cause infection. Those for continuous wear, which have recently been increasing in popularity, are particularly dangerous. Further, bacteria, fungi, etc. may grow on the surface of both hard and soft contact lenses in a lens container and even the lens container itself, sometimes causing corneal infectious diseases.

Water-containing soft contact lenses, while comfortable to apply, are susceptible to colonization by bacteria and fungi, both on the surfaces and within the body of the soft contact lenses because of their own hydrophilic properties, as well as their high water content. This colonization of lenses with bacteria and/or fungi can cause serious infectious diseases. Moreover, these contact lenses demand care in handling and the sterilization treatments are tedious.

Contact lenses are worn on the cornea of the eye to improve sight. Both hard and soft contact lenses require periodic cleaning and disinfecting to remove protein deposits and undesirable microbes from their surfaces. In most cases, the lens is removed from the eye, cleaned with a lens cleaning solution and subsequently disinfected. After disinfection, the lens usually is rinsed with saline solution before placement in the eye.

Disinfecting treatments should effectively disinfect the lens without causing toxicity to the eye. Thousands of compositions exist which are capable of disinfecting, but which exhibit toxic or undesirable discomfort to the eye when applied to lenses. Lens users sometimes fail to rinse the disinfectant solution from their lenses before placing back into their eyes. In some cases, lens wearers rinse their lenses poorly. Sometimes, the disinfecting composition adheres to or adsorbs into the lens itself, such that even after a rinse, the relatively toxic substances from the disinfectant solution may still be temporarily retained within the surface of the lens. When that occurs, the toxic substances may be released into the eye once the lens is re-inserted. For these reasons, a desirable disinfectant solution preferably does not contain any compositions in concentration levels that exceed toxicity limits for the eye.

One of the problems connected with soft contact lenses is the method used for their sterilization and cleaning. The very property of hydrophilic soft lenses which allows them to absorb up to 150 percent water by weight also allows preservatives, which might otherwise be used for cleaning and sterilization, to be absorbed and even concentrated before later release when the soft contact lens is on the eye. The release may be much slower than the uptake, which allows the preservative to build up in the lenses. This buildup eventually affects the physical characteristics of the lenses including dimension, color, etc. Additionally, buildup of preservatives can damage or stain the contact lens itself and/or ultimately harm the sensitive tissues of the conjunctivae or cornea.

Contact lenses are commonly worn on a daily basis and kept in a storage case/solution during the night hours or whenever they are not being worn. During wear and normal handling, microorganisms, as well as biomolecules such as lipids, proteins, etc. can adhere to contact lenses and thus be transferred to the storage case/solution. Furthermore, a tear film containing proteins, lipids, and even microorganisms, and represents the natural flora of the ocular surface, covers the surface of the eye. Any of the components found in the tear film, on the external surface of the eye, or the surrounding skin can be carried into the storage case/solution on the contact lens.

Some of the microorganisms that may be transferred from the eye or fingers to the storage case/solution may multiply therein, and may later be pathogenic to the human cornea or other ocular structures. When the contact lens is returned to the eye following its overnight soaking period, it is possible for these pathogens to be transferred to the surface of the eye. Although human tears contain natural antimicrobial agents, a pathogen-bearing lens in contact with the cornea of the eye can serve as a reservoir for infection that might overcome the eye's natural defenses. This is especially true for soft contact lens as the material tends to absorb the microorganisms. The result of microbial growth—bacterial, protozoan or even fungal—can cause damage to the eye resulting in impaired vision and even blindness. Therefore, contact lenses should be disinfected daily to remove pathogenic organisms. This is usually done overnight (six to eight hours) in order to protect the wearer's eyes from infection.

The method for evaluating the effectiveness of a disinfectant generally involves determination the agent's ability to reduce the numbers of viable organisms within the normal contact lens storage time between wearings (six to eight hours, i.e., "overnight"). This reduction of organism numbers is typically reported in terms of the change in the common log of the microbial population following exposure to the antimicrobial agent. For example, if the agent within a challenge solution has effected a reduction in a particular organism from $10^6$ colony forming units (cfu) per milliliter (ml) to $10^2$ cfu/ml within six hours of exposure the change, or "log reduction", would be reported as 4.0 (logs). In other words, the number of viable organisms has been reduced to one ten-thousandth of the original level.

These tests are most often performed by challenging the agent within solution with a concentrated viable inoculum (e.g., $10^5$-$10^6$ cfu/ml) of each test organism. Samples are withdrawn at different timepoints, plated on growth agar and the number of viable organisms determined by colony counts. Of particular interest is the duration of typical overnight storage of soft contact lenses. It should be apparent that such a challenge represents a worst case scenario since a far greater number of microbes is added than would ever be expected on a contact lens. Further, it should also be apparent that the results of the test may be significantly influenced by other components of the solution besides the disinfectant agent.

In the case of contact lens and ophthalmic solutions, various agents are added to enhance compatibility with the eye. To avoid stinging or irritation it is important that the solution possess a tonicity and pH within the physiological range, e.g., 200-350 mOsmol/L for tonicity, and 6.5-8.5 for pH. To this end, various buffering and osmotic agents are often added. The simplest osmotic agent is sodium chloride since this is a major solute in human tears. In addition, propylene glycol, lactulose, trehalose, sorbitol, mannitol or other osmotic agents may also be added to replace some or all of the sodium chloride. Also, various buffer systems such as citrate, phosphate (appropriate mixtures of $Na_2HPO_4$, $NaH_2PO_4$, and $KH_2PO_4$), borate (boric acid, sodium borate, potassium tetraborate, potassium metaborate and mixtures), bicarbonate, and tromethamine and other appropriate nitrogen-containing buffers (such as ACES, BES, BICINE, BIS-Tris, BIS-Tris Propane, HEPES, HEPPS, imidazole, MES, MOPS, PIPES, TAPS, TES, Tricine) can be used to ensure a physiologic pH between about pH 6.5 and 8.5. Under these circumstances, studies and development of contact lenses endowed with antimicrobial properties have been promoted.

Bacteria and fungi can also colonize contact lens-care articles, such as containers, to cause secondary infection. Therefore, it has been proposed that addition of an antimicrobial agent to the lens soaking solution, lens cleaner, or storage container may prevent microorganism growth.

Large quantities and/or high concentrations of antimicrobial agents can be toxic to the eye and the body. Hence, methods for controlling microorganisms that do not involve the addition of an antimicrobial agent have been studied. Resins coated with an antimicrobial substance have been proposed, but they are unsuitable for use with contact lens-care articles because they are extremely prone to leaching.

Where antimicrobial properties are imparted to a contact lens per se, special care for safety is required. This is because a contact lens comes into direct contact with the cornea and conjunctiva, and any substance eluted from the lens is carried by tears to the digestive tract. Accordingly, an antimicrobial substance that could be incorporated into contact lenses and/or related articles would be required to be highly active, heat stabile and to be firmly fixed to the lens so that it could not leach-out.

It should also be noted that the lens must exert the antimicrobial activity while retaining other properties essential to contact lenses, such as optical performance (i.e., transparency, uniformity, and heat stability), processability, strength, safety, and the like.

Contact lenses having inherently antimicrobial properties have been described. For instance, U.S. Pat. No. 5,515,117 (Dziabo) relates to contact lenses, and to contact lens cases having antimicrobial properties.

U.S. Pat. No. 5,520,910 (Hashimoto) describes that phosphonium salt type vinyl monomer graft-polymerized to the surface layer of a contact lens material imparts antimicrobial properties. In this case, a contact lens is subjected to a surface treatment, such as ultraviolet irradiation, corona discharge, or low-temperature plasma discharge, and the phosphonium salt type vinyl monomer is grafted to the radical so generated.

During wear, contact lenses are susceptible to the accumulation of proteinaceous materials that may adhere to the surface of the lens. Proteinaceous materials include, lysozyme, lactoferrin, albumin, and mucoproteins, and all constituents of lachrymal tears. Contact lenses that are repeatedly worn over an extended period of time must be cleaned to remove these materials as part of a routine care regimen.

If contact lenses are not properly cleaned, lysozyme, mucoproteins, and the like can accumulate on the lenses and may lead to the lens wearer experiencing discomfort or a loss of visual acuity. The presence of proteinaceous deposits may also decrease gas permeability and/or adversely affect the spectral characteristics of the lenses. Proteinaceous deposits may also block the efficacy of antimicrobials that are bound to the lens surface.

Fungal keratitis is a rare, but serious corneal infection that is sometimes associated with contact lens wear. In 2006, there was a sharp increase in the number of reported cases of *Fusarium* keratitis worldwide [Chang, D. C., et al, *JAMA* 296(8) p 953-963 (2006)].

In addition to contact lenses, other surfaces have been associated with colonization of bacteria, fungi, and other microbes. Examples of such surfaces include the surfaces of medical devices and health care equipment, food service items, general personal-use consumer goods, infant care items, kitchen and bathroom surfaces, as well as shared equipment. Bacteria, fungi, and other microbes can colonize on the surfaces especially when the surfaces are used in an environment that provides adequate moisture, favorable temperature, and suitable nutrients. If left untreated, surfaces can serve as a vehicle to transmit disease between individuals who may come in contact with the surfaces.

Disinfecting treatments are known in the art. However, many exhibit toxic or other undesirable characteristics that may preclude their use in a variety of circumstances. For example, bleach is an effective antimicrobial. But its use on some surfaces can have a negative impact on the surface itself. Residual bleach on the surface of a medical device, such as a syringe, can be toxic to individuals who use the syringe or may react with medicines drawn into the syringe. Similarly, residual bleach on infant care items, such as bottles or cribs, could negatively impact the health of an infant who comes in contact with the item.

Methods of binding quaternary ammonium polymers to surfaces are well known in the art. U.S. Patent Application Publication Nos. 2002/0177828 A1 and 2005/0033251 A1 as well as U.S. Pat. Nos. 7,045,673 B1, 7,151,139 and 6,146,688 and International Patent Application WO 2007/024974 A3 disclose various methods of binding quaternary ammonium polymers to impart antimicrobial activity to certain surfaces. These patents, patent applications and publications are incorporated by reference herein.

There are a variety of methods to bond quaternary ammonium polymers to surfaces. Cellulose, ceramic, metal, or polymeric materials with hydroxyl groups or available reactive carbons on their surfaces can be used as a substrate for the cerium (IV) and other initiator catalyzed grafting reactions. The extent of grafting will be dependent on the surface hydroxyl concentration and the concentration of susceptible carbon atoms. Even materials which do not normally contain sufficient surface hydroxyl groups may be used as substrates, as many methods are available for introducing surface hydroxyl groups. These methods generally include hydrolysis or oxidation effected by methods such as heat, plasma-discharge, e-beam, UV, or gamma irradiation, peroxides, acids, ozonolysis, or other methods. It should be noted that methods other than cerium initiated grafting may also be used in the practice of this invention.

In addition to cerium, azo compounds such as AIBN (2,2'-azobisisobutyronitrile) are commonly used as initiators for vinyl polymerizations, but are not generally thought of as catalysts for preparation of graft copolymers. We have found, however, that a water-soluble derivative of AIBN (2,2'-Azobis[N-(2-carboxyethyl)-2-methylpropionamidine]tetrahydrate, or VA-057, available from Wako Specialty Chemicals) was a suitable initiator for the graft polymerization of quaternary vinyl monomers onto cellulosic substrates such as paper or onto starch substrates. AIBN, which is one of the most commonly used polymerization initiators, is not soluble in water, and thus cannot be used directly in aqueous solutions. AIBN is soluble in alcohols, however, and thus can possibly be used as an initiator for the graft polymerization of quaternary monomers onto cellulose since the monomers are also soluble in alcohols. It is also likely that AIBN could be used in an emulsion system in order to achieve similar results. Other potentially useful Azo initiators include: (2,2'-Azobis[2-(5-methyl-2-imidazolin-2-yl)propane]dihydrochloride, or VA-041; 2,2'-Azobis (2-methyl-N-[1,1-bis(hydroxymethyl)-2-hydroxyethyl]propionamide, or VA-080; 2,2'-Azobis(2-methylpropionamide) dihydrochloride, or V-50; 2,2'-Azobis (N-cyclohexyl-2-methylpropionamide), or Vam-111; 1,1'-Azobis(cyclohexane-1-carbonitrile); and numerous other similar compounds). Organic peroxides such as benzoyl peroxide (BPO) are also widely used as polymerization initiators. Just as in the case of AIBN (above), BPO is not water soluble, but it can possibly be used in alcoholic solution in order to graft quaternary vinyl monomers onto cellulose. Other potentially useful peroxide initiators include: (dicumyl peroxide, t-butyl peroxide, methylethylketone peroxide, and a variety of other peroxides, peroxyketals, peroxydicarbonates, and hydroperoxides). These and numerous other potentially useful catalysts are available from a variety of suppliers such as Lucidol-Penwalt, and Akzo. Combinations of two or more of the initiators described above are also effective. These catalysts or initiators can also be used to form crosslinked cellulose-quaternary grafted materials.

Alternatively, the cationic polyelectrolytes may also be applied via non-catalyzed methods. For example, an antimicrobial polymer can be applied to a substrate as an aqueous solution followed by a drying step. It is also possible to utilize mixed solvents, such as water/alcohol mixtures, for initial application of the antimicrobial to the substrate using the described process, combined with a drying step. This will depend on the solubility of the antimicrobial in the mixed solvent systems. For instance, mixtures of alcohol and water may be used. It may also be possible to use completely non aqueous solvent systems; however, it is necessary that the antimicrobial be soluble in the chosen solvent system.

It is known in the art that quaternary ammonium polymers that are bound to surfaces can impart a certain degree of antimicrobial efficacy and biofilm-resistance to the surfaces. U.S. Patent Application Publication Nos. 2002/0177828 A1 and 2005/0033251 A1 and U.S. Pat. Nos. 7,151,139 and 6,146,688 disclose methods of binding quaternary ammonium polymers to impart antimicrobial activity to surfaces. Other examples of quaternary ammonium compounds used to impart antimicrobial efficacy are discussed below.

U.S. Pat. No. 4,675,347 (Mochizuki et al.) describes an antimicrobial latex composition comprising a cationic natural rubber latex and an inorganic or organic salt of a quaternary ammonium compound. Citrate is listed as one of the many examples of suitable salts. The cationic antimicrobial agent is incorporated in the latex and has a long "pot life". The antimicrobial agent is released in a controlled manner at a constant rate. The composition may be used in gloves, tubes, finger sacs, catheters, sponges, mattresses, bath mats, rubber cloth, binders, fabrics, footwear soles, ice bags, etc.

U.S. Pat. No. 6,534,075 (Hei et al.) describes sanitized substrates having residual antimicrobial activity which contain compositions comprising a quaternary amine, an oxidant, a halide source, and pH buffers (including citrate). Compositions are effective on substrates such as those used in food transport lines, liquid filtration equipment, filtering agents, belt sprays, storage facilities, air circulation systems, aseptic packaging, refrigerators and coolers, cutting boards, sinks, beverage chillers, garments, animal quarters, microbes on eggs, animal skins, etc.

U.S. Pat. No. 6,702,983 (Hu et al.) describes a method for inhibiting the attachment of microorganisms to biomaterial surface, such as a contact lens, with a solution of a composition comprising a cationic polysaccharide polymer which may further comprise a quaternary ammonium and antimicrobial groups. The cationic biomaterial may be covalently bound to the surface of the biomaterial, but it is not critical. Control of the ionic strength of the solutions unexpectedly affects the performance of the cationic cellulose polymer. Many substances, including citrate can be used to control the pH of the solution.

U.S. Pat. No. 7,001,873 (McDonnell et al.) describes an alkaline cleaner for prion infected surfaces such as medical and surgical instruments, pharmaceutical and food preparation facilities, floors, work surfaces, equipment, cages, tanks, and fluid lines. The cleaner comprises an anti-redeposition agent such as a citrate salt and a cationic polymer such as polyDADMAC.

While the above-mentioned art describe the use of quaternary ammonium compounds for use as antimicrobial agents, none describes the use of such compound in conjunction with a citrate treatment to enhance the antimicrobial effectiveness of the resulting compositions. It is an aspect of the present invention that the antimicrobial and biofilm resistance effects of the combining quaternary ammonium and citrate is greater than the sum of the effect of the individual components.

SUMMARY OF THE INVENTION

Industrial Application

One embodiment of the invention pertains to contact lenses with cationic polyelectrolytes nonleachably bound to a surface of the lens material, in order to impart antimicrobial efficacy. It has been found that the antimicrobial performance (efficacy and duration of antimicrobial activity and resistance to biofilm formation) of such surface can be significantly enhanced by storage of a lens in certain solutions.

This enhanced performance persists even after removal of the lens from the storage solution and subsequent rinsing with saline solution.

In a preferred embodiment of the invention, the storage solution contains citrate ion in a concentration of at least 5 mM (millimolar), up to 50 mM. The formula weight of trisodium citrate is 258 g/mol, so 1 mM trisodium citrate is approximately a 0.025 weight % solution, 5 mM citrate is approximately 0.125%, and 50 mM trisodium citrate is approximately a 1.25 weight % solution.

In a more preferred embodiment of the invention, the storage solution contains citrate in concentration of at least 10 mM, and in an even more preferred embodiment of the invention, the storage solution contains citrate in concentration of at least 15 mM.

In the practice of this invention, the citrate may be combined with the nonleachably bound polycationic antimicrobial after the substrate has been previously treated with the polycationic antimicrobial; however, it is also within the scope of this invention to treat a substrate simultaneously with the polycationic antimicrobial and the citrate ion, for instance by combining citrate ion with a cationic polymerizable monomer, or with a polycationic material, and then treating the substrate to effect binding in a nonleachable manner.

Another embodiment of the invention pertains to other surfaces with cationic polyelectrolytes nonleachably bound to the surfaces in order to enhance, increase, or prolong the antimicrobial and biofilm-resistant efficacy of the treated surface. Examples of surfaces that this embodiment pertains to includes medical devices and other health care equipment, food service items, general personal-use consumer items, infant care items, kitchen and bathroom surfaces, shared equipment, textiles, and any other surface in need of antimicrobial protection. Antimicrobial and biofilm-resistant efficacy of these surfaces can be enhanced by rinsing, brushing, dipping, wiping, or spraying the antimicrobial surfaces with citrate solution and allowing the citrate to dry onto the surfaces.

In a preferred embodiment of the invention pertaining to other surfaces, a citrate concentration of at least 0.1% is preferred and a citrate concentration of at least 0.5% is more preferred.

Definitions

Enhancement agent: An additive to an aqueous contact lens storage solution that enhances the antimicrobial efficacy and increases the biofilm resistance of antimicrobial lenses stored in the storage solution. An example of an enhancement agent is citrate.

Antimicrobial efficacy: A measure of the ability to reduce the number of viable microorganisms within a given time period. The reduction in microorganisms is measured as the change in the common log of the microbial population following exposure to an antimicrobial agent. As shown in the examples presents below, the antimicrobial efficacy of antimicrobial contact lenses is found to diminish over time when kept in a contact lens storage solution that does not contain citrate, such as phosphate buffered saline.

Non-leaching: The property of remaining in place instead of dispersing into a surrounding liquid medium. In the context of this disclosure, it refers to the ability of the antimicrobial agent or agents in or on antimicrobial contact lens, or other surface as disclosed herein, to remain in or on the lens or surface instead of escaping into a surrounding lens storage solution, tear fluid, aqueous washes, or other solutions that may come in contact with the lens or substrate.

Surface: The interface between a solid substrate and the atmosphere or a liquid. Where the solid substrate is a hydrogel or is porous, the "surface" includes areas within the outer boundaries of the substrate.

DETAILED DESCRIPTION OF THE INVENTION

One invention pertains to a system and method of enhancing the efficacy of inherently antimicrobial contact lenses. More specifically, it pertains to enhancing the antimicrobial efficacy of contact lenses which have cationic polyelectrolytes nonleachably bound to the surface of the contact lens. Even more specifically it pertains to enhancing the antimicrobial efficacy of contact lenses which have quaternary ammonium polymers bound to the surface on the lens. Most specifically, it pertains to enhancing the antimicrobial efficacy of contact lenses which have poly(diallyldimethylammonium chloride) (also known as polyDADMAC) graft polymerized onto the surface of the lens.

As described above, it is known in the art to include quaternary ammonium compounds and polymers into contact lenses in order to provide antimicrobial properties to the lens. Furthermore, it is known to covalently bond antimicrobial agents such as quaternary ammonium polymers to the lens in order to provide extended and non-leaching antimicrobial properties. One skilled in the art will appreciate that the antimicrobial efficacy of the lens is expected to increase as the content of antimicrobial in the lens increases. Thus, a given composition (or concentration of active agent) would be expected to provide a certain degree of antimicrobial efficacy, either in actual use conditions, or in experiments designed to model actual use conditions. The systems and methods described herein pertain to contact lenses which have been surface modified to contain quaternary ammonium groups. When these lenses are exposed to, or stored in solutions of specific composition, an unexpected enhancement of the antimicrobial efficacy is observed, without increasing the content of antimicrobial agent in the lens. In particular, storage of contact lenses surface grafted with poly(diallyldimethylammonium chloride) are found to have significantly increased antimicrobial efficacy when stored for relatively short periods of time in solutions that contain citrate ion.

Contact lenses were modified by surface grafting of quaternary ammonium polymers, including poly(DADMAC). These modified lenses were found to exhibit significant antimicrobial activity; however, it was observed that after several weeks of storage in PBS (phosphate buffered saline) solution, the antimicrobial efficacy became diminished. This initiated a search for a more suitable storage solution for the treated lenses, and the eventual discovery that citrate storage solution not only helped maintain antimicrobial efficacy of the lenses over time, but also improved efficacy. This observed effect may be due to chelation of calcium from the bacterial cell walls, which may weaken the bacteria, and allow for the poly(DADMAC) to exert enhanced antimicrobial efficacy. However, it is to be understood that the invention is not limited to any one particular mode of action as other modes of action may be applicable to explain the observed effect.

First, several commercially available lens cleaning/storage solutions were tested as alternative storage solutions. It was discovered that storing the treated lenses in Alcon's Opti-Free® Express® allowed for efficacy to be maintained for at least one month after treatment.

Next, the individual components of the Opti-Free solution, which include EDTA, boric acid, AMP-95™ (aminomethylpropanol, trademark of Angus Chemical) and sodium citrate were tested. It was discovered that citrate solution appeared to exhibit a synergistic effect with the polyDADMAC-coated lenses, leading to improved antimicrobial efficacy.

Citric acid is used as a preservative in foods and other commercial products; however, it does not show potent antimicrobial activity such as that exhibited by quaternary ammonium compounds. The antimicrobial effect of citric acid is predominately based on the acidic pH imparted to the formulation, and this effect would be negated in applications where low pH is not acceptable. It would be expected that storage of lenses in solutions of antimicrobial compounds, such as quaternary ammonium compounds, would produce an enhanced antimicrobial effect; however, such an effect is not to be expected from storage of lenses in solutions containing low levels of citrate ion. Indeed, unmodified lenses (lenses without antimicrobial polymer attached) stored in identical solutions did not show any antimicrobial effect (see examples below). That the synergistic effect of the combination of quaternary ammonium antimicrobial polymers bound to the lens, and exposure of those lenses to citrate-containing solutions results in enhanced antimicrobial properties is an unexpected and useful discovery.

Citrate is defined as the fully and partially-neutralized conjugate bases of citric acid ($C_6H_8O_7$), which have an ionic charge of either negative 3 (−3), known as "tribasic citrate", with the molecular formula ($C_6H_5O_7$); negative 2 (−2), known as "dibasic citrate" ($C_6H_6O_7$), or negative 1 (−1), known as "monobasic citrate" ($C_6H_7O_7$). Any of these forms of citrate, may be utilized in the practice of this invention. It will be recognized by one skilled in the art that citric acid and the three forms of citrate ion all coexist in solution and interchange by a chemical equilibrium which is influenced by pH.

Citrate may be employed in the practice of this invention in the form of any soluble citrate salt. Generally, the counterion will be an alkali metal such as lithium, sodium, or potassium; an alkaline earth such as magnesium; other metal ion; or an organic cation. The sodium and potassium salts are preferred. When citric acid or citric acid solutions are utilized in the practice of this invention, at least a portion of the citric acid will spontaneously be converted to citrate ion in solution when the pH is above approximately 2. Since the general utility of this invention will be in applications requiring a neutral pH (approximately 5 to 9), the citrate will generally exist in predominately the dibasic or tribasic form.

Testing of the antimicrobial efficacy in of the lenses during incubation in artificial tear fluid is a more challenging test method than simply testing in PBS solution, because of the possibility of deposition of proteinaceous material which could block efficacy of the surface-bound antimicrobial groups. As the examples below will show, storage of the antimicrobial lenses in citrate solutions increased the antimicrobial efficacy even in the presence of artificial tear fluid.

In addition to contact lenses, the invention also pertains to a system and method of enhancing the antimicrobial and biofilm-resistant efficacy of inherently antimicrobial surfaces which have cationic polyelectrolytes nonleachably bound to the surface. Such surfaces included the surfaces of contact lens cases, eyeglass cases, eyewear, medical devices and health care equipment, food service items, general personal-use consumer goods, infant care items, kitchen and bathroom surfaces, shared equipment, textiles; and any other surface in need of antimicrobial protection. It is preferred that the cationic polyelectrolyte is a quaternary ammonium polymer. It is more preferred that the cationic polyelectrolyte is a poly (diallyldialkyl ammonium salt), and it is most preferred that the cationic polyelectrolyte is poly(diallydimethyl ammonium chloride), also known as polyDADMAC polymerized onto the surface.

Specific examples of surfaces that the invention pertains to are the surfaces of medical devices and health care equipment including devices used in cardiovascular, respiratory, and urological care such as catheters, tracheal tubes and other tubing, endoscopic and other diagnostic devices, blood reservoirs, filters and containers, surgical tools, operating room tables, mayo stands, service trays, surgical equipment trays, pharmacy preparation surfaces, air and liquid handling devices, etc.; food services items including plates, trays, silverware, prep tables and counters, serving tables and counters, stands, and vending machines; general personal-use consumer goods including prescription pill containers, toothbrush holders, denture storage containers, hearing aids, and athletic bandages; infant care items including formula bottles, high chairs, changing tables, cribs, playpens, and other infant-contact surfaces; kitchen and bathroom surfaces including counters, countertops, sinks, toilets, toilet seats, bidets, appliances, stovetops, ovens, microwaves, refrigerators, cabinets, tiles, tubs, shower walls, faucets, floors, baseboards, shower curtains, and bathtub mats; shared equipment including shopping carts, telephones, fax machines, copy machines, computer terminals, table tops, filing cabinets, desk tops, public transit seats, guardrails, keyboards, doorknobs, facet handles, mailboxes, and automotive interior surfaces; textiles; and any other surface in need of antimicrobial protection which would be known to one skilled in the art.

Typically these surfaces can be comprised of a polymer, metal, ceramic, plastic, rubber glass, textile, gel, hydrogel, painted surface, cellulose, or other solid to which a polyquaternary antimicrobial may be attached.

Any of the above-mentioned surfaces may be modified by treating it to effect binding of quaternary ammonium polymer to said surface. This may be accomplished by methods known in the art, such as treatment with an alkoxy silane-quaternary compound (such as DC5700, made by Dow Corning), or by graft polymerization of unsaturated quaternary ammonium monomers, such as DADMAC, onto the surface as described in US Patent Application Publication 2002/0177828 A1, or U.S. Pat. No. 7,151,139, or by formation of an interpenetrating network such as described in U.S. Pat. No. 6,146,688, or by any other suitable method.

This binding of quaternary ammonium polymer to said surface will impart a certain degree of antimicrobial efficacy and biofilm resistance to said surface. This antimicrobial and biofilm-resistant effect can be enhanced, increased, or prolonged by subsequent exposure of the modified surface to a solution of citrate ion in water. The citrate ion may be incorporated into the polycationic antimicrobial by a variety of means of applying the citrate. For example, a means for applying the citrate may be by brushing, dipping, wiping, or spraying solutions of the citrate onto a surface. Alternatively, a means for applying the citrate to a contact lens can be by storing or soaking the lens in a solution of citrate ion. A contact time of greater than a minute will generally be sufficient. The citrate may be applied as a sodium salt, or in another form. When applied as a sodium salt, the di-sodium or tri-sodium citrate form is preferred. A citrate concentration of at least 0.1% is preferred, a citrate concentration of at least 0.50% is more preferred. The object may be dried directly after treatment with citrate ion, or the object may be rinsed with water prior to drying. Alternatively, the object may be dried, rinsed with water, and then redried.

Exposure of the modified surface to citrate ion serves to replace all or part of the anionic counterions to the quaternary ammonium cations (which are normally chloride), with citrate ions. After treatment with citrate ion, the modified surface will be found to have improved antimicrobial efficacy, and improved biofilm adhesion resistance, due to a synergistic effect between the quaternary ammonium polymer and the citrate ion. The citrate-modified surface may be recharged as necessary to replenish the antimicrobial and anti-biofilm effects, by repeating the exposure to citrate.

It is known in the art to incorporate citrate into solutions used to store contact lenses, disinfect surgical instruments, food preparation surfaces, and cages, inhibit attachment of microorganisms to biomaterial surfaces, impart residual antimicrobial activity to cutting boards, sink, garments, animal skins, and latex. However, citrate is generally added as a pH buffer component and not to provide any antimicrobial effect. Citrate has also been added to solutions for use as an antioxidant, anti-redeposition agent, buffering agent, humectant, sequestering agent, and wetting agent. But there has been no disclosure of citrate incorporated in any of these solutions to provide any antimicrobial effect. There is no prior disclosure of a separate citrate treatment of antimicrobial surface to enhance their antimicrobial or biofilm-resistant efficacy. Thus, it is unexpected that the presence of citrate provides a significant increase in antimicrobial efficacy of the contact lenses that have been surface modified by grafting of quaternary ammonium polymers. It is also unexpected that a citrate treatment would provide enhanced antimicrobial or biofilm-resistant efficacy on a variety of surfaces. Citrate is a natural substance, and is non-irritating and nontoxic.

In light of the general disclosure provided herein above, with respect to the manner of practicing this invention, those skilled in the art will appreciate that this disclosure enables the practice of the invention as defined in the following claims. The following experimental details are provided to ensure a complete written description of this invention, including the best mode thereof. Each example below is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in or are obvious from the following detailed description. It is to be understood by one of ordinary skill in the art that the present discussion is a description of exemplary embodiments only, and is not intended as limiting the broader aspects of the present invention, which broader aspects are embodied in the exemplary constructions.

Many alterations and modifications may be made by those having ordinary skill in the art without departing from the spirit and scope of the present invention. The words used to describe the invention and its various embodiments are to be understood not only in the sense of their commonly defined meanings, but to include by special definition in this specification structure, material or acts beyond the scope of the commonly defined meanings. Thus if an element can be understood as including more than one meaning, then its use must be understood as being generic to all possible meanings supported by the description and by the word itself. The definitions of the words or elements of the following aspects are, therefore, defined in this specification to include not only the combination of elements which are literally set forth, but all equivalent structure, material or acts for performing substantially the same function in substantially the same way to obtain substantially the same result.

EXAMPLES

Example 1

Standard Method for in-situ Graft Polymerization of Diallyldimethylammonium Chloride (DADMAC) onto Contact Lens Example 1 describes the standard method for in situ polymerization of diallyldimethylammonium chloride (DAD-MAC) onto silicone hydrogel contact lenses. It establishes efficacy of the treated lenses versus *Pseudomonas aeruginosa* in a standard microbiology protocol as compared with untreated control lenses. The example describes a specific assay where the polyDADMAC-treated lenses were tested for antimicrobial activity after storage in one of four different concentrations of citrate solution for seven days and gives results in tabular form. Included in the table is a lens stored in a 'zero' citrate concentration solution (PBS) for one week, and its resulting lower efficacy. This establishes that storage of the lenses in citrate solution increases efficacy of the poly-DADMAC-treated lenses.

Acuvue® Oasys™ with Hydraclear™ Plus (Lot B0045NQ) Senofilcon-A lenses were removed from sterile packaging and submerged in individual 10 mL glass vials containing 3 mL of argon-sparged monomer solution [0.15 g VA-085 initiator (2-2'-Azobis {2-methyl-N-[2-(1-hydroxybutyl)]propionamide}, Wako Chemicals, Lot K2010), 0.3 g distilled water, 3.0 g diallydimethylammonium chloride, 65% aqueous solution (DADMAC) (Aldrich, Batch #16126P0)]. Vials were sealed under argon and lenses were soaked in the monomer solution for 30 minutes at room temperature before being heated in an 80° C. oven for 2 hours. The vials were removed from the oven, cooled, uncapped and submerged in 5 L of dilute (3 mM) sodium citrate solution and soaked for 18 hours. Lenses were removed from the vials and soaked in fresh sodium citrate solution for two hours. This was repeated one more time. The lenses were then transferred to individual 50 mL conical centrifuge tubes containing 10 mL of sterile 12 mM, 15 mM, 25 mM or 50 mM sodium citrate solution (pH adjusted to 7.2 using 0.25M citric acid) and autoclaved at 121° C. for 20 minutes. The lenses prepared by this method are referred to in subsequent examples and discussion as "treated lenses".

Microbiology Protocol for Example 1

Verification of antibacterial efficacy was determined using the standardized protocol described below. Three treated lenses from each concentration of sodium citrate storage solution and three untreated (as received) lenses were rinsed three times in three separate 15 mL NUNC conical centrifuge tubes containing 10 mL of sterile 1×PBS (Fisher catalog #BP300-1, Phosphate Buffered Saline, 10× solution, pH 7.4±0.1 (1×)). Fifteen wells of a sterile 24-well tissue culture plate were filled with 300 µL of thawed, sterile "tear-like fluid". "Tear-like fluid" is a phosphate-buffered composition containing bovine proteins and lipids made to simulate natural human tear fluid. A single lens was aseptically transferred to each well and examined to ensure that it was properly oriented, laying flat in the well and not folded onto itself. The well-plate was placed on a distilled-water moistened paper towel inside a sealed plastic rectangular container and incubated for approximately 18 hours at 35° C. while shaking at 100 rpm.

A culture of *Pseudomonas aeruginosa* (ATCC #15422) from stock was grown overnight in 100 mL of tryptic soy broth in a 37° C. shaker incubator, aerated by shaking at 100 rpm. The bacteria were transferred to four 50 mL conical centrifuge tubes (25 mL in each) and centrifuged at 3500 rpm for 10 minutes. The supernatant was decanted and the pellets were re-suspended in 10 mL of PBS and pooled into one 50 mL conical centrifuge tube. This washing step was repeated two more times for a total of three washes. The final pellet was re-suspended in 10 mL of PBS. A standardized inoculum was prepared by adding 110 µL of the washed suspension to a sterile vessel containing 9 mL of PBS. The optical density of the inoculum was measured at 0.24 OD at 595 nm on a Spectronic 20 spectrophotometer. A working inoculum was prepared by diluting 200 μL of the standardized (0.24 OD) inoculum in 19.8 mL of PBS. The working inoculum was serially diluted and plated to determine the actual inoculum concentration using a standard spread plate method. This was determined to be $1.4 \times 10^6$ CFU/mL.

Lenses were removed from the tear-like fluid and rinsed three times in three separate vessels containing 100 mL of sterile PBS. Fifteen wells of a sterile 24-well tissue culture plate were filled with 1 mL aliquots of the working inoculum. A single lens was aseptically transferred to each well and examined to ensure that it was properly oriented, laying flat in the well and not folded onto itself. The tissue culture plate was placed in the shaker incubator (37° C.) and shaken at 100 rpm for two hours. The lenses were washed by immersing each lens five times in three consecutive vessels containing 100 mL of PBS. Lenses were released into each vessel and the forceps were sterilized and flamed between transfers to new vessels. The lenses were aseptically transferred to individual sterile 50 mL conical centrifuge tubes containing 10 mL of 0.05% Tween 80 in PBS. The tubes were secured in triplicate and vortexed at the highest speed for 3 minutes. The tubes were then sonicated for two minutes in a water-bath sonicator filled with 1-inch of water.

The supernatant in these tubes was marked as the $10^{-4}$ dilution of the microorganism removed from the contact lens. Serial dilutions were made and plated using a standard pour plate technique to enumerate the viable bacteria in the supernatant. Following approximately 48 hours of incubation at 35° C., the plates were counted and recorded.

The average number of colonies on the plates of the three control lenses was $6.27 \times 10^4$ CFU. This was determined by counting the number of colonies on each $10^{-3}$ dilution plate and averaging the three numbers. The results for the treated lenses are listed in Table 1 below:

TABLE 1

| Citrate Storage Solution Concentration | Average Log Reduction* | Average Percent Reduction** |
|---|---|---|
| 0 mM (12 mM PBS) | 1.15 | 92.21% |
| 12 mM | 3.80 | 99.98% |
| 15 mM | 4.13 | 99.99% |
| 25 mM | 3.97 | 99.83% |
| 50 mM | 3.44 | 99.87% |

*Log Reduction was calculated by finding the difference of the log of the average number of colonies counted on the $10^{-3}$ dilution plates for the three control lenses and the log of number of colonies counted on the $10^{-1}$ dilution plate of each treated lens. The reported Average Log Reduction is the average of the log reductions for each set of three treated lenses. See equations below.
Log Reduction 1 = $LOG_{10}$ {(CFUs on Control plate 1 + CFUs on Control plate 2 + CFUs on Control plate 3) ÷ 3} − $LOG_{10}$ (CFUs on Treated plate 1).
Average Log Reduction = {(Log Reduction 1 + Log Reduction 2 + Log Reduction 3) ÷ 3}.
**Average Percent Reduction was calculated by subtracting from one the ratio of the average number of colonies counted on the $10^{-1}$ dilution plates of each set of three treated lenses to the average number of colonies counted on the $10^{-3}$ dilution plates of the three control lenses. The difference is reported as a percentage.

Example 2

Assay to Determine Antimicrobial Efficacy of Treated Lenses versus *Staphylococcus aureus*

Example 2 describes treated lenses stored in 12 mM citrate solution and their efficacy versus a gram positive organism, *Staphylococcus aureus*. Six lenses treated as described above in Example 1, stored in 12 mM sodium citrate, and six untreated control lenses were tested for bactericidal efficacy versus *Staphylococcus aureus* (ATCC #6538) using the protocol described in Example 1. The working inoculum concentration (0.245 OD at 595 nm) was serially diluted and plated to determine the actual inoculum concentration of $1.09 \times 10^7$ CFU/mL by a standard spread plate method. The average number of colonies counted on the $10^{-3}$ dilution plates for the six control lenses was $2.60 \times 10^4$ CFU. The average log reduction by the treated lenses was 3.03 (99.84% reduction).

Example 3

Loss of Antimicrobial Efficacy of Treated Lenses when Stored in PBS

Example 3 demonstrates the loss of efficacy of treated lenses versus *Pseudomonas aeruginosa* over time when stored in PBS containing no citrate ion. Tests were run immediately after treatment, again after one week, and again after two weeks.

Lenses were prepared by the method described above in Example 1, but stored in three different solutions following their final rinse. Lenses were placed in individual 50 mL centrifuge tubes containing 15 mL of a particular storage solution. Nine lenses were placed in tubes containing 15 mL of PBS, nine lenses were placed in tubes containing 15 mL of PBS with 0.1% polyDADMAC and nine lenses were placed in tubes containing 15 mL of PBS with 0.25% polyDADMAC and autoclaved at 121° C. for twenty minutes. The treated lenses and three control (as received unmodified) lenses were tested by the microbiology protocol described in Example 1 two days after lens preparation, then again one week, and again two weeks after preparation. Results for the testing two days after preparation indicated that all of the lenses were equally effective with a 99.7% reduction in bacterial colonies versus the control lenses. Antimicrobial lens efficacy declined in the test performed one week after preparation with only 95.1% fewer bacterial colonies for the lenses stored in PBS versus the control lenses. The test performed two weeks after preparation resulted in 92.2% fewer bacterial colonies for the lenses stored in PBS versus the control lenses. The addition of the pDADMAC homopolymer to the storage solutions did not significantly deter the loss of efficacy of the lenses. This demonstrates the loss in efficacy of treated lenses stored in the absence of citrate.

Example 4

Assay to Verify Antimicrobial Efficacy of Treated Lenses

Experiments were run to determine if treated lenses originally stored in citrate solution, then moved to other storage solutions, would maintain efficacy. Example 4 is included to establish efficacy of a particular batch of treated lenses initially stored in 15 mM sodium citrate. Antimicrobial contact lenses with quaternary ammonium groups nonleachably bound to the lenses were prepared by the method described above in Example 1. All lenses were transferred to individual 50 mL conical centrifuge tubes containing 15 mM sodium citrate solution (pH adjusted to 7.3 using 0.25M citric acid). Antibacterial efficacy was verified using the protocol described in Example 1. The working inoculum (0.27 OD at 595 nm) of *Pseudomonas aeruginosa* (ATCC #15442) was serially diluted and plated to determine the actual inoculum concentration using a standard spread plate method. This was determined to be $4.9 \times 10^6$ CFU/mL. The average number of colonies counted on the $10^{-3}$ dilution plates for the three control lenses was $3.91 \times 10^4$ CFU. The average number of colonies counted on the $10^{-1}$ dilution plates for the three treated lenses was $1.37 \times 10^{1}$ CFU. The difference in the number of colonies translates to a 3.77 log reduction (99.965%) in the bacterial population, compared to non-antimicrobial (unmodified) lenses.

Example 5

Assay to Compare Efficacy of Treated Lenses After Storage in Various Solutions—Alcon Opti-Free® Solution Example 5 describes testing of treated lenses stored in Opti-Free Express (OF), a commercially-available citrate-containing lens storage solution. Samples included in this assay are described in Table 2 below.

TABLE 2

| Description of Contact Lenses Included in Assay | Average Log Reduction |
| --- | --- |
| Three untreated, as received contact lenses, included as experimental controls. | N/A |
| Three untreated contact lenses stored in Opti-Free solution for 7 days. | −0.08 |
| Three treated contact lenses stored in 15 mM sodium citrate solution for 17 days. | 3.77 |
| Three treated contact lenses stored in 15 mM sodium citrate solution for 9 days, then asceptically transferred to Opti-Free solution and stored for 7 days. | 3.18 |
| Three treated contact lenses stored in Opti-Free solution for 17 days. | 4.34 |

The results show that all treated lenses stored in Opti-Free Express and 15 mM sodium citrate solutions retained efficacy versus *Pseudomonas aeruginosa*. After storage in 15 mM sodium citrate for nine days, three treated lenses, as described in Example 4, were transferred to individual 50 mL conical centrifuge tubes containing 10 mL of sterile Alcon Opti-Free® Rinsing, Disinfecting and Storage Solution (Lot 60459F, Expiration 2009-07). The label describes this solution as "a sterile, buffered, isotonic, aqueous solution containing a citrate buffer system and sodium chloride with edentate disodium and POLYQUAD (polyquaternium-1) 0.001% as a disinfecting agent." Three untreated, as received control lenses were transferred from their sterile packaging to Opti-Free solution. All six lenses were stored for one week and then were tested for efficacy using the microbiology protocol of Example 1. Also included in the assay were three treated lenses that were stored in 15 mM sodium citrate for 17 days, since treatment, and three treated lenses that were stored in Opti-Free for 17 days, since treatment on the same day. The standard control plates had an average count of $4.67 \times 10^{4}$ CFU. Control populations for both sets of untreated lenses were not significantly different. Treated lenses stored in Opti-Free since preparation had an average log reduction of 4.34 (99.99% reduction). The lenses stored in 15 mM sodium citrate solution since preparation had an average log reduction of 3.77 (99.96% reduction). The lenses transferred from 15 mM sodium citrate to Opti-Free solution had an average log reduction of 3.18 (99.91% reduction). All treated lenses stored in Opti-Free Express and 15 mM sodium citrate solutions retained efficacy versus *Pseudomonas aeruginosa*.

Example 6

Assay to Compare Antimicrobial Efficacy of Treated Lenses After Storage in Various Solutions—Borate-Buffered Saline Solution Example 6 describes testing of treated lenses as described in Example 5, but with borate-buffer solution (non-citrate) instead of Opti-Free solution. The results show that treated lenses stored initially in 15 mM sodium citrate followed by transfer to borate-buffered saline were more effective versus *Pseudomonas aeruginosa* than were treated lenses stored in the borate-buffered saline since preparation. The assay described above in Example 5 was repeated using a borate-buffered saline solution, which contains boric acid, sodium borate, sodium chloride, deionized water, EDTA and methyl ether cellulose, (but not citrate) instead of the Alcon Opti-Free® solution. Again, the control populations for both sets of untreated lenses were not significantly different. The average number of colonies counted on the $10^{-3}$ dilution plates for the standard controls was $1.26 \times 10^{4}$ CFU. The treated lenses stored in 15 mM sodium citrate solution for 23 days, since preparation, had an average log reduction of 3.23 (99.89% reduction). The treated lenses stored in borate-buffered saline for 23 days, since preparation, had an average log reduction of only 1.63 (97.43% reduction). The lenses that were first stored in 15 mM sodium citrate, then transferred to borate-buffered saline for nine days, had an average log reduction of 2.77 (99.79%). Treated lenses stored initially in 15 mM sodium citrate followed by transfer to borate-buffered saline were more effective versus *Pseudomonas aeruginosa* than were treated lenses stored in the borate-buffered saline since preparation. The beneficial effect of citrate treatment is clearly demonstrated.

Example 7

Antimicrobial Efficacy of Treated Lenses Against Fungal Organisms

Treated lenses prepared according to Example 1 were tested for antimicrobial efficacy against the fungal organism *Fusariam solani*. A standardized dilution (32,000 CFU/ml) of freshly cultured *Fusariam* was prepared in sterile saline. 1.5 ml of this standardized inoculum was added to each well of a 12-well tissue culture plate. Using sterile techniques, treated lenses and control contact lenses were separately added to individual inoculated wells. The wells were observed for growth daily for 10 days. Carryover and adherence of organisms was determined by removing and washing the contact lenses after the 10-day incubation. The wash solution was added to BHI broth and observed for growth after 6 days. Washings from treated lenses did not demonstrate any growth after 6 days (as evidenced by clear cultures). In contrast, the washings from control lenses were positive for growth (cloudy culture) after 6 days. Adherence of *Fusariam* to the contact lenses was specifically explored by incubating the washed contact lenses in water overnight (to force the organisms into "survival" mode) followed by transfer to BHI broth and incubation for 5 days. Washed treated lens cultures remained clear and therefore did not demonstrate any growth after 5 days. However, the control washed lens culture was cloudy and thus was positive for growth after 5 days. These results demonstrate that treated lenses do not support the growth of *Fusariam* and can prevent carry over and transfer of *Fusariam* to other vehicles.

Example 8

A General Method for Enhancing the Antimicrobial Activity of a Surface Derivitized with Quaternary Ammonium Groups A surface of an object, such as a toothbrush handle, toilet seat, medical device, doorknob, or the like is modified by treating it to effect binding of quaternary ammonium polymer to said surface. This may be accomplished by methods known in the art, such as treatment with an alkoxy silane-quaternary compound (DC5700-Dow Corning), or by graft polymerization of unsaturated quaternary ammonium monomers, such as DADMAC, onto the surface as described in U.S. Patent Application 20020177828, or U.S. Pat. No. 7,151,139, or by formation of an interpenetrating network such as described in U.S. Pat. No. 6,146,688, or by any other suitable method. The binding of quaternary ammonium polymer to said surface will impart a certain degree of antimicrobial efficacy and biofilm resistance to said surface. This antimicrobial and biofilm-resistant effect can be enhanced, increased, or prolonged by subsequent exposure of the modified surface to a dilute solution of citrate ion in water. The citrate ion may be applied by brushing, dipping, wiping, or spraying. A contact time of one minute will generally be sufficient. The citrate may be applied as a sodium salt, or in another form. When applied as a sodium salt, the di-sodium or tri-sodium citrate form is preferred. A citrate concentration of at least 0.10% is preferred, a citrate concentration of at least 0.50% is more preferred. The object may be dried directly after treatment with citrate ion, or the object may be rinsed with water prior to drying. Alternatively, the object may be dried, rinsed with water, and then redried. Exposure of the modified surface to citrate ion serves to replace all or part of the anionic counterions to the quaternary ammonium cations (which are normally chloride), with citrate ions. After treatment with citrate ion, the modified surface will be found to have improved antimicrobial efficacy, and improved biofilm adhesion resistance, due to a synergistic effect between the quaternary ammonium polymer and the citrate ion. The citrate-modified surface may be recharged as necessary to replenish the antimicrobial and anti-biofilm effects, by repeating the exposure the citrate.

Example 9

Textile Treatment Using polyDADMAC and Citrate

Cotton jersey substrates were treated with two different solutions and tested for antimicrobial efficacy using the standard AATCC 100 method. Two treatment solutions were prepared for treatment of 100% cotton knit jersey substrates. The first solution was 1.0 weight % aqueous poly(diallyldimethyl ammonium chloride). The second solution was 0.94 weight % aqueous poly(diallyldimethyl ammonium chloride) and 0.06 weight % citric acid. Solutions were padded onto the cotton substrates using a roller press at 100% wet pickup. Substrates were then dried in an 80° C. oven for two hours. Substrates were tested using the standard AATCC 100 method for antibacterial efficacy versus *Staphylococcus aureus* (ATCC #6538). The samples treated with the PD only showed a 2.05±0.74 log reduction of viable bacteria compared to untreated controls. The samples treated with the combination of PD and citric acid showed a 5.48±0.00 log reduction of viable bacteria compared to untreated controls.

Particular embodiments of the present invention, both a system and method, are set forth as follows. The present invention includes a system to enhance the antimicrobial efficacy of contact lenses during a period of storage comprising contact lenses with cationic polyelectrolytes nonleachably bound to the surface of the lenses to impart antimicrobial activity to the lenses; and a lens storage case containing the lenses, and an aqueous solution comprising an enhancement agent. It is an aspect of this invention that in a preferred embodiment, the cationic polyelectrolytes are quaternary ammonium polymers. In an even more preferred embodiment, the quaternary ammonium polymers are poly(diallyldimethylammonium chloride). Also, in a preferred embodiment of this system, the enhancement agent comprises citrate in a concentration of about 0.125 weight % to about 1.25 weight % solutions.

Another embodiment of the present invention is a method for storing antimicrobial contact lenses in a solution which enhances the antimicrobial efficacy of the lenses and which prevents a loss of the antimicrobial properties of the lenses which may occur when said lenses are stored in other types of solutions. In one embodiment of this method, the steps comprise: (a) providing in sterile packaging at least one contact lens with cationic polyelectrolytes bound or grafted to the surface of each contact lens; (b) removing each contact lens from the sterile packaging; (c) providing a lens storage case containing an aqueous storage solution comprising an enhancement agent; (d) immersing each contact lens into said aqueous storage solution in said storage case; and (e) storing each contact lens within the storage case and aqueous storage solution for an amount of time sufficient to enhance the antimicrobial efficacy of each contact lens. In a preferred embodiment of this method the cationic polyelectrolytes in step (a) are quaternary ammonium polymers. In a more preferred embodiment the quaternary ammonium polymers in step (a) are poly(diallyldimethylammonium chloride). Also, in a preferred embodiment, of the method above, the enhancement agent of step (c) comprises citrate in a concentration ranging from about 0.125 weight % to about 1.25 weight % solutions.

Although the invention has been described in detail with particular reference to the above preferred embodiments, other embodiments for enhancing the antimicrobial efficacy of contact lenses might achieve the same results and this disclosure is not meant in any manner to be limiting. Variations and modifications of the present invention are possible and it is intended that all such variations, modifications and equivalents are covered in the above aspects of the invention. The entire disclosures of all references set forth above, and of the corresponding application, are hereby incorporated by reference in their entirety.

We claim:
1. A method of enhancing the antimicrobial efficacy and biofilm resistance of a contact lens having a quaternary ammonium polymer nonleachably bonded to a surface thereof comprising the steps in sequence of,
  a. providing an aqueous solution comprising an effective amount within the range of 5 mM to 50 mM of a citrate enhancement agent and
  b. immersing said contact lens in said aqueous solution for at least one minute,
  whereby the antimicrobial efficacy and biofilm resistance of said contact lens is enhanced as compared to that of an otherwise identical contact lens not immersed in said aqueous solution, and wherein the antimicrobial efficacy and biofilm resistance is evidenced by a magnitude of at least 2.75 log when tested for efficacy versus *Pseudomonas aeruginosa*.

2. The method of claim 1, wherein said quaternary ammonium polymer is a poly(diallyldialkylammonium) polymer.

3. The method of claim 2, wherein said quaternary ammonium polymer is poly(diallyldimethylammonium chloride), also known as polyDADMAC.

4. The method of claim 2, wherein said aqueous solution comprises said citrate enhancement agent in a concentration within the range of 10 mM to 50 mM.

5. The method of claim 2, wherein said aqueous solution comprises citrate in a concentration within the range of 15 mM and 50 mM.

6. The method of claim 1, further comprising the step of c. rinsing said contact lens with an aqueous saline solution.

7. A method of enhancing the antimicrobial efficacy and biofilm resistance of an antimicrobial solid surface having a quaternary ammonium polymer nonleachably bonded thereto comprising the steps in sequence of,
   a. providing an aqueous solution comprising an effective amount within the range of 5 mM to 50 mM of citrate ion and
   b. applying said aqueous solution to said antimicrobial solid surface, whereby the antimicrobial efficacy and biofilm resistance of said antimicrobial solid surface is enhanced as compared to that of an otherwise identical antimicrobial solid surface to which said aqueous solution has not been applied, and wherein the antimicrobial efficacy and biofilm resistance is evidenced by a magnitude of at least 2.75 log when tested for efficacy versus *Pseudomonas aeruginosa*.

8. The method of claim 7, further comprising the step of c. drying said antimicrobial solid surface.

9. The method of claim 8, further comprising the steps of
d. rinsing said antimicrobial solid surface with water, and
e. drying said antimicrobial solid surface.

10. The method of claim 7, further comprising the steps of
c. rinsing said antimicrobial solid surface with water, and
d. drying said antimicrobial solid surface.

11. The method of claim 7, wherein said aqueous solution is applied by brushing on, dipping in, storing in, wiping onto, or spraying onto said antimicrobial solid substrate.

12. The method of claim 7, wherein said antimicrobial solid surface is a surface of a contact lens case, an eyeglass case, eyewear, a medical device or other health care equipment, a food service item, a general personal-use consumer item, an infant care item, a kitchen or bathroom surface, shared equipment, or a textile.

13. The method of claim 7, wherein said quaternary ammonium polymer is poly(diallyldimethylammonium chloride), also known as polyDADMAC.

14. The method of claim 7, wherein said aqueous solution comprises said citrate ion in a concentration within the range of 10 mM to 50 mM.

15. The method of claim 7, wherein said aqueous solution comprises citrate ion in a concentration within the range of 15 mM to 50 mM.

* * * * *